US012576273B2

(12) United States Patent
Song et al.

(10) Patent No.: US 12,576,273 B2
(45) Date of Patent: Mar. 17, 2026

(54) TREATMENT SYSTEM USING VAGUS NERVE STIMULATION AND OPERATING METHOD THEREOF

(71) Applicant: NEURIVE Co., Ltd., Gimbae-si (KR)

(72) Inventors: Jae Jun Song, Seoul (KR); Hyuk Choi, Seoul (KR); Guk Han Kim, Anyang-si (KR); Yong Ho Jung, Incheon (KR)

(73) Assignee: NEURIVE Co., Ltd., Gimbae-si (KR)

( * ) Notice: Subject to any disclaimer, the term of this patent is extended or adjusted under 35 U.S.C. 154(b) by 917 days.

(21) Appl. No.: 17/792,570

(22) PCT Filed: Dec. 16, 2021

(86) PCT No.: PCT/KR2021/019180
§ 371 (c)(1),
(2) Date: Jul. 6, 2023

(87) PCT Pub. No.: WO2023/113073
PCT Pub. Date: Jun. 22, 2023

(65) Prior Publication Data
US 2024/0189591 A1 Jun. 13, 2024

(51) Int. Cl.
*A61N 1/36* (2006.01)
*A61N 1/04* (2006.01)

(52) U.S. Cl.
CPC ....... *A61N 1/36031* (2017.08); *A61N 1/0456* (2013.01); *A61N 1/0472* (2013.01); *A61N 1/36034* (2017.08)

(58) Field of Classification Search
None
See application file for complete search history.

(56) References Cited

U.S. PATENT DOCUMENTS

| | | | | |
|---|---|---|---|---|
| 2018/0133507 A1* | 5/2018 | Malchano | .......... | A61N 1/36082 |
| 2021/0379374 A1* | 12/2021 | Hamner | .............. | A61N 1/0502 |

FOREIGN PATENT DOCUMENTS

| | | |
|---|---|---|
| JP | 10-108913 A | 4/1998 |
| JP | 2019-51021 A | 4/2019 |

(Continued)

OTHER PUBLICATIONS

International Search Report dated Sep. 1, 2022 in Application No. PCT/KR2021/019180.

(Continued)

*Primary Examiner* — Carl H Layno
*Assistant Examiner* — Bryan Mcallister Lee
(74) *Attorney, Agent, or Firm* — Sughrue Mion, PLLC

(57) ABSTRACT

Proposed is a treatment system using vagus nerve stimulation. The treatment system includes a treatment part including an electrode configured to be worn on at least one of the left and right ears and configured to generate electrical stimulation on the vagus nerve in the auricle, a controller configured to transmit an electrical stimulation signal for generating the electrical stimulation to the treatment part, an input part configured to allow a user to input user information, and a measurement part configured to measure biometric information on the user. The controller adjusts an intensity and a pattern of the electrical stimulation on the basis of the biometric information measured by the measurement part, and adjusts a treatment protocol including treatment time and treatment intensity on the basis of the biometric information measured by the measurement part and the user information input by the input part.

19 Claims, 7 Drawing Sheets

(56)        References Cited

FOREIGN PATENT DOCUMENTS

| KR | 10-0596540 | B1 | 7/2006 |
| KR | 10-2012-0135321 | A | 12/2012 |
| KR | 10-2013-0031174 | A | 3/2013 |
| KR | 10-2014-0095291 | A | 8/2014 |
| KR | 10-1468355 | B1 | 12/2014 |
| KR | 10-1756723 | B1 | 7/2017 |
| KR | 10-2017-0132277 | A | 12/2017 |
| KR | 10-2019-0088300 | A | 7/2019 |

OTHER PUBLICATIONS

Written Opinion of the International Searching Authority dated Sep. 1, 2022 in Application No. PCT/KR2021/019180.
Notice of Allowance dated Jan. 17, 2023 from the Korean Patent Office in Application No. 10-2020-0156234.

* cited by examiner

TREATMENT SYSTEM USING VAGUS NERVE STIMULATION AND OPERATING METHOD THEREOF

TECHNICAL FIELD

The present disclosure relates to a system for treating a disease and, more particularly, to a system for treating a disease by stimulating the vagus nerve.

BACKGROUND ART

The vagus nerve is one of the cranial nerves and is also called the 10th cranial nerve. The vagus nerve runs from the brain through the face and thorax to the abdomen. It is a mixed nerve that contains parasympathetic fibers and is involved in the regulation of parasympathetic nerves acting on the heart, lungs, and digestive tract. It has the longest and most complex of the 12 pairs of cranial nerves, and contains both sensory and motor nerve fibers.

It is known that a vagus nerve stimulator for the treatment of epilepsy and depression has been approved by the US Food and Drug Administration (FDA), and it targets the cervical branch of the vagus nerve located in the neck. However, this electrical stimulation of the cervical branch of the vagus nerve is a surgical procedure involving making an incision in the skin to expose the cervical branch of the vagus nerve, winding a coil, which is an electrical body, around the cervical branch, and grafting a microchip therein. Thus, it cannot be used in the field of self-treatment by the general public.

In oriental medicine, a method of treating diseases by ear acupuncture has been used. Since the ear is where the auricular branch of the vagus nerve is located, it can be said that the principle of ear acupuncture therapy is based on stimulation of the vagus nerve.

Accordingly, a device for electrically stimulating the vagus nerve distributed in the ear has been developed, but it is not widely used because of individual differences in sensitivity to stimulation and differences in treatment effect.

DISCLOSURE

Technical Problem

Accordingly, the present disclosure has been made keeping in mind the above problems occurring in the related art, and an objective of the present disclosure is to provide a treatment system capable of applying an individually optimized treatment protocol to a user.

Technical Solution

In order to achieve the above objective, according to one aspect of the present disclosure, there is provided a treatment system using vagus nerve stimulation, the treatment system including: a treatment part including an electrode configured to be worn on at least one of the left and right ears and configured to generate electrical stimulation on the vagus nerve in the auricle; a controller configured to transmit an electrical stimulation signal for generating the electrical stimulation to the treatment part; an input part configured to allow a user to input user information; and a measurement part configured to measure biometric information on the user. The controller may adjust an intensity and a pattern of the electrical stimulation on the basis of the biometric information measured by the measurement part, and adjust a treatment protocol including treatment time and treatment intensity on the basis of the biometric information measured by the measurement part and the user information input by the input part.

The measurement part may measure brainwaves of the user, and the controller may adjust the intensity and pattern of the electrical stimulation on the basis of the measured brainwaves. The controller may perform fast Fourier transform (FFT) analysis on the brainwaves, and adjust a dose of the intensity, the pattern, etc. of the electrical stimulation on the basis of the amount of change in the brainwaves obtained by comparing a composition ratio of the brainwaves composed of delta waves, theta waves, alpha waves, beta waves, and gamma waves.

The measurement part may measure a heart rate of the user, and the controller may adjust the intensity and pattern of the electrical stimulation on the basis of the measured heart rate. The controller may adjust the intensity of the electrical stimulation by comparing heart rate variability with a reference value.

The user information may include disease information related to a disease and other general information, the disease information may include first disease information on an intensity and a frequency of symptoms input while the electrical stimulation is applied and second disease information as other disease-related information, and the controller may adjust the treatment protocol on the basis of the first disease information. A treatment process may be composed of a plurality of sessions, and the treatment protocol of a subsequent session may be adjusted on the basis of the first disease information input by the user in a previous session.

The treatment part may further include an acoustic device configured to generate a sound, and the controller may transmit a sound signal to the acoustic device, and the controller may derive a hearing loss pattern and a hearing loss frequency on the basis of the information input by the user in a state in which a sound is applied, and adjust an attenuation frequency and a width of a bandpass filter for treatment of hearing loss.

The treatment system may further include an environment measurement part configured to measure surrounding environment information. The controller may adjust the treatment protocol by converting the surrounding environment information measured by the environment measurement part into a stress index. The environment measurement part may be installed in a wearable device.

The measurement part may be installed in the treatment part worn on the user's ear or may be installed in a wearable device.

According to another aspect of the present disclosure, there is provided a method of operating a treatment system using vagus nerve stimulation, the method including: an information collecting step of inputting by a user, user information on an intensity and a frequency of symptoms in a state in which stimulation for diagnosis is applied to the user's body through an electrode that is configured to be worn on at least one of the left and right ears and configured to generate electrical stimulation, and then measuring biometric information of the user; a treatment program designing step of determining an intensity and a pattern of the electrical stimulation on the basis of the measured biometric information and determining a treatment protocol including treatment time and treatment intensity on the basis of the biometric information measured by a measurement part and the user information input by an input part, and; a treatment step of stimulating the vagus nerve by applying a designed treatment program to the electrode.

According to another aspect of the present disclosure, there is provided a treatment system using vagus nerve stimulation, the treatment system including: a treatment part including an electrode configured to be worn on at least one of the left and right ears and configured to generate electrical stimulation on the vagus nerve in the auricle; a controller configured to transmit an electrical stimulation signal for generating the electrical stimulation to the treatment part; an input part configured to allow a user to input user information; a measurement part configured to measure biometric information on the user; and a server configured to send and receive data to and from the controller. The server may adjust an intensity and a pattern of the electrical stimulation on the basis of the biometric information measured by the measurement part, and adjust a treatment protocol including treatment time and treatment intensity on the basis of the biometric information measured by the measurement part and the user information input by the input part to transmit the adjusted treatment protocol to the controller.

The server may adjust the intensity, the pattern, and the treatment protocol of the electrical stimulation through an artificial intelligence (AI)-based algorithm.

The server may provide a diagnosis stimulation protocol and a treatment stimulation protocol.

The server may provide video and sound content for diagnosis and video and sound content for treatment.

The server may provide video and sound content for training.

The server may be connected to a medical terminal used by an expert and may adjust the intensity, the pattern, and the treatment protocol of the electrical stimulation through the medical terminal. The medical terminal may display personal information and disease-related information of the user.

Advantageous Effects

According to the present disclosure configured as describe above, by reflecting information on a disease input by a user in a state in which stimulation for diagnosis or treatment is applied, and measured biometric information and surrounding environment information of the user, together with general personal information of the user and general information on the disease, it is possible to construct a treatment protocol optimized for the user or modify the treatment protocol so as to be optimized.

Figure 1:
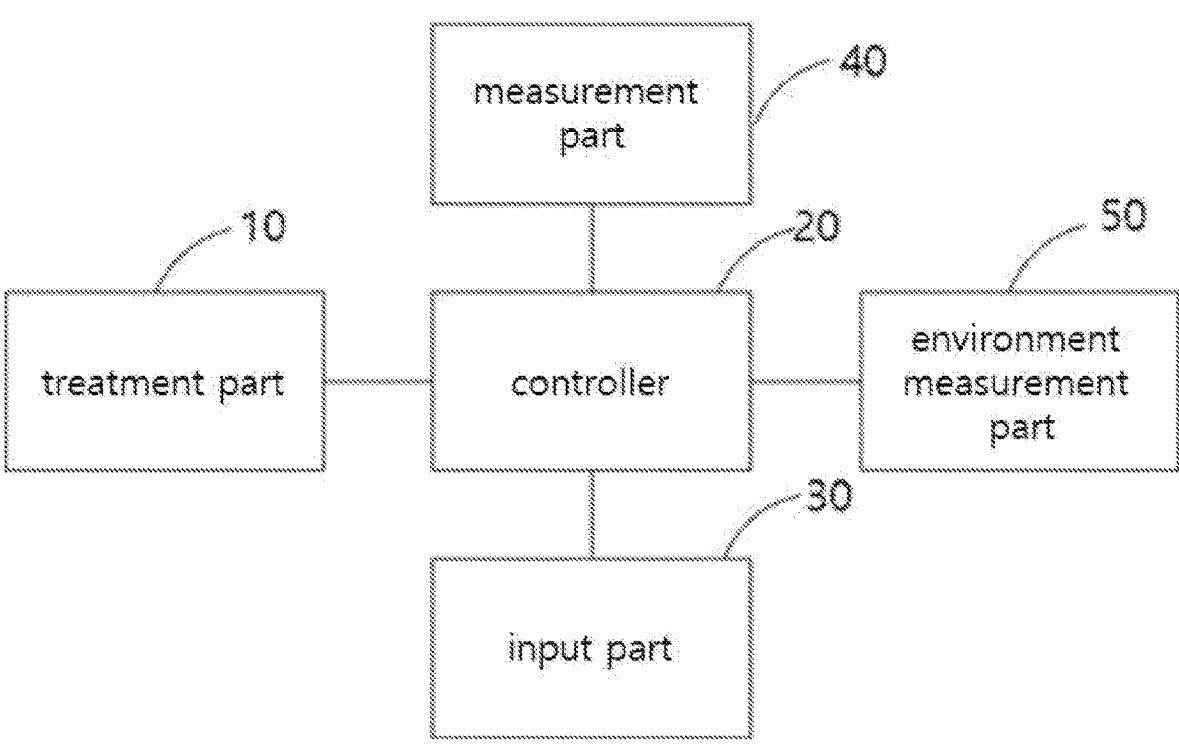
FIG. 1 is a schematic view illustrating the configuration of a treatment system using vagus nerve stimulation according to an embodiment of the present disclosure.

[Description of the Reference Numerals in the Drawings]

| | |
|---|---|
| 10: treatment part | 20: controller |
| 30: input part | 40: measurement part |
| 50: environment measurement part | |
| 100: treatment device part | 200: first server |
| 300: second server | |

MODE FOR INVENTION

Reference will now be made in detail to an exemplary embodiment of the present disclosure, examples of which are illustrated in the accompanying drawings.

Various changes to the following embodiment are possible and the scope of the present disclosure is not limited to the following embodiment. In the drawings, the shape and size of elements may be exaggeratedly drawn to provide an easily understood description of the structure of the present disclosure. Wherever possible, the same reference numerals will be used throughout the drawings and the description to refer to the same or like elements or parts.

Also, when an element is referred to as being "connected" to another element, it can be "directly connected" to the other element or can be "electrically connected" to the other element with one or more intervening elements therebetween. It will be understood that terms such as "comprise", "include", and "have", when used herein, specify the presence of stated features, integers, steps, operations, elements, components, or combinations thereof, but do not preclude the presence or addition of one or more other features, integers, steps, operations, elements, components, or combinations thereof.

Further, the terms "first", "second", etc. may be used herein to describe various elements, but these elements should not be limited by these terms. These terms are only used to distinguish one element from another element. For instance, a first element discussed below could be termed a second element, and the second element could also be termed the first element.

FIG. 1 is a schematic view illustrating the configuration of a treatment system using vagus nerve stimulation according to an embodiment of the present disclosure.

The treatment system using vagus nerve stimulation according to the embodiment includes a treatment part 10, a controller 20, an input part 30, a measurement part 40, and an environment measurement part 50.

The treatment part 10 is a component that applies stimulation for treatment to a user.

Since the present disclosure aims to apply electrical stimulation to the vagus nerve in the ear, the treatment part 10 is worn on the ear, and for example, may be worn on at least one of the left ear and the right ear or may be worn on both ears. The wearing method thereof is not particularly limited, and various methods may be adopted. When the treatment part 10 is worn on both ears, the same type of electrical stimulation may be applied to both ears, but different types of electrical stimulation may be applied to the left ear and the right ear. The intensity, frequency, and pattern, etc. of electrical stimulation may be modified, and the intensity, frequency, or pattern of electrical stimulation applied to the left ear and the right ear may be given differently. This is because the present disclosure adjusts electrical stimulation to suit the user.

An electrode for applying electrical stimulation to the vagus nerve in the ear is provided. At least one electrode is installed to be brought into contact with the auricle including the external acoustic meatus and the helix. In addition to the electrode for electrical stimulation, a device for applying other stimulation for treatment may be further provided. For example, a sound device that applies acoustic stimulation to the user may be provided together. The sound device may reproduce a sound source for sound therapy such as tinnitus treatment, and may reproduce a sound source such as music or natural sound for stabilizing the mind and body of the user during an electrical stimulation treatment process. Furthermore, when the treatment part 10 is worn on both ears, the same sound and the same type of electrical stimulation may be applied to both ears, but different types of stimulation may be applied to the left ear and the right ear. In this case, the dose of each stimulation may be varied. Since the present disclosure adjusts stimulation to suit the user, it is possible to perform treatment suitable for each user on the basis of the results measured for the left and right ears.

The controller 20 is a component that transmits an electrical stimulation signal for generating electrical stimulation to the electrode of the treatment part.

In the present disclosure, electrical stimulation for treatment or diagnosis is applied to the vagus nerve in the ear through the electrode. The electrical stimulation signal is configured to reflect the intensity of stimulation and the pattern to which stimulation is applied. The controller 20 stores information on the electrical stimulation signal and transmits the same to the treatment part 10 so that electrical stimulation is performed by the electrode. In this case, a general controller can only transmit a predetermined electrical stimulation signal to the electrode of the treatment part and modify the overall intensity of the electrical stimulation signal. However, in the present disclosure, the controller 20 can not only modify the partial intensity and the pattern of the electrical stimulation signal, but also modify a treatment protocol including treatment time and treatment intensity. Specific details of adjusting the electrical stimulation signal or treatment protocol will be described later.

When the treatment part 10 further includes the device for applying other stimulation for treatment in addition to the electrode for electrical stimulation, the controller 20 transmits a stimulation signal corresponding to the device. Specifically, when the sound device is provided together, the controller 20 may store and transmit information on an acoustic stimulation signal for a sound source for sound therapy, and may store and transmit information on an acoustic stimulation signal for a sound source such as music or natural sound for stabilizing the mind and body of the user during the electrical stimulation treatment process. In particular, the frequency at which acoustic stimulation applied for the treatment of tinnitus may be adjusted, and the attenuation frequency of sound for the treatment of hearing loss and the width of a bandpass filter may be adjusted.

The controller 20 may be included in the same device as the treatment part 10, or may be included in an external device separated from a treatment device in which the treatment part 10 is installed. The external device may be connected to the treatment device by wire or wirelessly to send and receive signals or data. The external device may be configured as a dedicated device in which a program or application for the treatment system is installed, or may be installed in the form of a program or application in a smart device.

The input part 30 is a component that allows the user to input information.

Information that may be input by the user through the input part 30 may be divided into disease information related to a disease and other general information. The general information is information corresponding to unique information of the user, including age, gender, weight, disease history, drug use history, life log, etc. These are information that is not directly related to the disease to be treated, but may be reflected in the process of constructing the treatment protocol. The disease information is information directly related to the disease to be treated, and may be divided into first disease information on the intensity and frequency of symptoms or changes in symptoms input by the user while electrical stimulation for treatment or diagnosis is applied to the vagus nerve and second disease information on the general intensity, frequency, and symptoms of the disease. The second disease information serves as a basis for selecting the basic construction of the treatment protocol and stimulation for diagnosis. The first disease information is used in the process of constructing a customized treatment protocol suitable for each user. The first disease information may be measured while adding stimulation for treatment or diagnosis in addition to the stimulation through the electrode. For example, a hearing loss pattern and hearing loss frequency may be derived on the basis of information input by the user in a situation in which acoustic stimulation for diagnosing hearing loss is applied. Based on this, the controller 20 may construct acoustic stimulation in which the attenuation frequency and the width of the bandpass filter are adjusted for the treatment of hearing loss, and may modify the construction of the acoustic stimulation for the treatment of hearing loss by reflecting information according to the user's input during the treatment of hearing loss. In addition, a sound source capable of increasing the efficiency of the electrical stimulation treatment process may be selected or constructed.

As in the case of the controller 20, the input part 30 may be included in the same device as the treatment part 10, or may be included in an external device separated from the treatment device in which the treatment part 10 is installed. Furthermore, even when included in the external device, the input part 30 may be included in the same device as the controller 20 or may be included in a separate device from the controller 20.

The measurement part 40 is a component that measures biometric information of the user.

The biometric information includes brain waves, heartbeat, blood pressure, etc. These information change in value by reflecting a physical and psychological state of the user. In particular, in a situation in which electrical stimulation or acoustic stimulation for diagnosis or treatment is applied, changes in the brain waves, heartbeat, blood pressure, etc. reflect subtle changes in the physical and psychological state that the user is not aware of.

The present disclosure can reflect not only the first disease information directly input by the user in a state in which stimulation for diagnosis or treatment is applied, but also directly acquire and reflect the user's biometric information, thereby providing a completely personalized treatment protocol that reflects changes in the body that the user is not aware of. In addition, changes in the body can be detected and immediately reflected during the treatment process in which stimulation is repeated, so that treatment can proceed within a range that does not put any strain on the body.

When the measurement part 40 measures the brainwaves of the user and transmits the same to the controller 20, the controller may perform fast Fourier transform (FFT) analysis on the brainwaves, and derive the composition ratio of alpha waves among the brainwaves to determine the amount of change in the alpha waves. The alpha waves are brainwaves with a frequency range of about 8 to 13 Hz, and appear when a person is in a relaxed state with eyes closed, a passive state, and an unconscious state. A decrease in the ratio of the alpha waves means an increase in anxiety or stress, and the dose of the intensity, pattern, etc. of electrical stimulation and/or reproduced music or sound may be adjusted accordingly. Furthermore, besides alpha waves, delta waves (1 to 3 Hz) related to the immune system, theta waves (3.5 to 8 Hz) related to depressive disorder, beta waves (12 to 33 Hz) related to concentration, and gamma waves (25 to 100 Hz) highly related to cognitive processing may be considered, and a suitable electrical stimulation intensity and pattern or music may be applied. In particular, the dose of the intensity, the pattern, etc. of electrical stimulation and music may be adjusted on the basis of the amount of change in each type of brainwaves obtained by comparing the composition ratio of the delta waves, theta waves, alpha waves, beta waves, and gamma waves.

When the measurement part 40 measures the heart rate of the user and transmits the same to the controller 20, the controller 20 compares the measured heart rate with a heart rate in a normal state and detects a change amount. The controller 20 compares heart rate variability with a reference value and modifies the intensity and pattern of electrical stimulation accordingly.

In addition, the measurement part 40 may be configured in various devices and forms to measure various biometric information that can reflect the user's physical and psychological state.

As in the case of the controller 20 and the input part 30, the measurement part 40 may be included in the same device as the treatment part 10, and may obtain biometric information through a device worn on the ear. In addition, the measurement part 40 may be included in an external device separated from the treatment device in which the treatment part 10 is installed, and in particular, may be manufactured in the form of a wearable device worn on various parts of the body or may be connected to the wearable device to measure the user's biometric information and transmit the same to the controller 20. The measurement part 40 may be composed of a plurality of measuring devices separated from each other. The plurality of measuring devices may be installed in one device or may be installed separately in a plurality of different devices.

The environment measurement part 50 is a component that measures surrounding environment information of the user.

The surrounding environment information is information such as temperature, humidity, fine dust, noise, light brightness, location, etc. The surrounding environment information may affect the manifestation of symptoms of the disease or the psychological state of the user. Unlike a place where the treatment environment is controlled, such as a hospital, in a place to which the treatment system according to the present disclosure is applied, the surrounding environment is not controlled. The influence of the surrounding environment affects the treatment effect. In addition, the change in the user's biometric information measured by the measurement part 40 may be due to stimulation applied by the treatment part 10, but may be a result of reflecting the influence of the surrounding environment. Thus, it is preferable to reflect information on the surrounding environment together.

In the present disclosure, the environment measurement part 50 measures information on the surrounding environment and transmits the same to the controller 20, and the controller 20 quantifies the surrounding environment information by converting the same into a stress index for the user, and reflects the stress index in the treatment protocol. This can further improve the therapeutic effect.

As in the case of the measurement part 40, the environment measurement part 50 may be included in the same device as the treatment part 10, and may measure information through a device worn on the ear. In addition, the environment measurement part 50 may be included in an external device separated from the treatment device in which the treatment part 10 is installed, and in particular, may be manufactured in the form of a wearable device worn on various parts of the body or may be connected to the wearable device to measure the surrounding environment information. The environment measurement part 50 may be composed of a plurality of measuring devices separated from each other. The plurality of measuring devices may be installed in one device or may be installed separately in a plurality of different devices.

Figure 2:
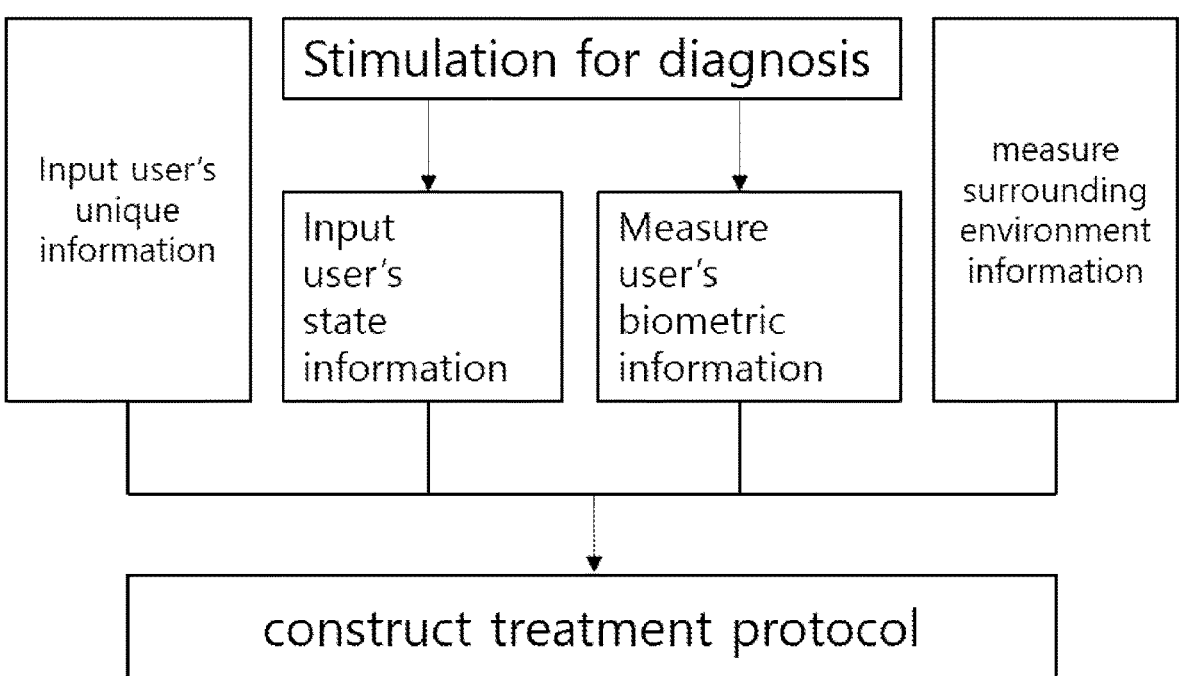
FIGS. 2 and 3 are schematic views illustrating the operation of the treatment system using vagus nerve stimulation according to the embodiment of the present disclosure.
Figure 3:
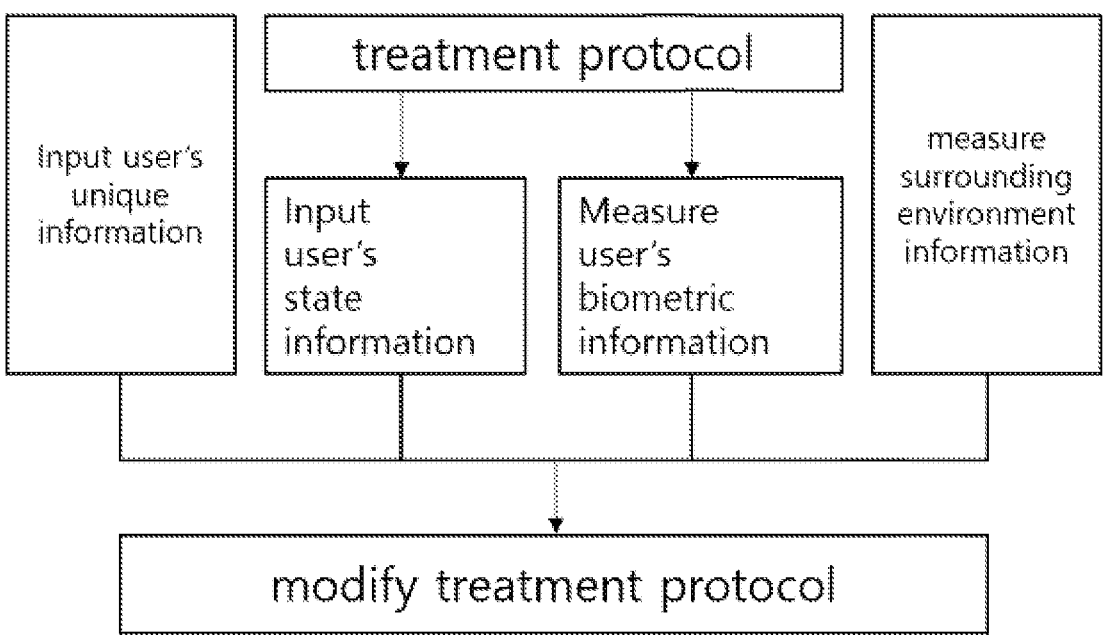

FIGS. 2 and 3 are schematic views illustrating the operation of the treatment system using vagus nerve stimulation according to the embodiment of the present disclosure.

FIG. 2 illustrates a case in which the treatment protocol is constructed at the initial stage of use of the treatment system. FIG. 3 illustrates a state in which the treatment protocol is modified to suit the user in the process of using the treatment system.

In the process of using the treatment system using vagus nerve stimulation according to the present embodiment, the user's unique information is input. The user's unique information may be input each time it is used. However, it is preferable to create a personal account and store the user's unique information for each individual account to use the user's unique information without a separate input. The user's unique information may include age, gender, weight, disease history, drug use history, life log, etc. These are general information that is not directly related to the disease to be treated, but are reflected in the process of constructing the treatment protocol at the initial stage of use. For example, one may be selected from among a plurality of types of diagnostic stimulation on the basis of age, gender, and weight, and these age, gender, and weight may be reflected in the process of configuring the treatment protocol such as treatment intensity, treatment time, construction of treatment sequence, and number of repetitions of sessions. In addition, the user's unique information may also be reflected when modifying the treatment protocol to the user's preferences during treatment.

The user's unique information may include information on general intensity, frequency, and symptoms of the disease to be treated. On the basis of the information on the disease input by the user, a basic treatment protocol may be constructed or stimulation for diagnosis may be constructed or selected.

The treatment system using vagus nerve stimulation according to the present embodiment constructs the treatment protocol by reflecting state information input by the user and the user's biometric information measured by the measurement part in the process of applying stimulation for diagnosis to the user. The stimulation for diagnosis may be constructed in the same way as the stimulation for treatment, but may be specially constructed to accurately diagnose the condition of the disease. The stimulation for diagnosis may be variously constructed depending on the disease to be treated. In the case of a disease such as hearing loss or tinnitus, the pattern of hearing loss or the frequency of hearing loss may be more accurately derived or a sound range in which tinnitus occurs may be derived through the user's state information input while electrical stimulation is applied alone or together with acoustic stimulation using sounds and through the measured biometric information of the user.

The state information input by the user may be symptoms, the intensity and frequency of symptoms, etc. The user directly measures and inputs a specific state of the disease in real time while the stimulation for diagnosis is applied to the vagus nerve. Thus, it is possible to more accurately diagnose a disease state of the user, and to construct the treatment protocol by reflecting this. Thereafter, the user directly inputs his or her state in real time while the stimulation by the treatment protocol is applied to the vagus nerve, and to modify the current treatment protocol or modify the treatment protocol to be performed in the future by reflecting this. This makes it possible to perform optimal treatment by not fixing the initial treatment protocol, but changing the treatment protocol as the treatment proceeds. Also, it is possible to optimize the treatment protocol for the user by receiving real-time feedback during the treatment process without performing a new diagnosis every time to modify the treatment protocol. The stimulation for diagnosis and input of the user's state according to the stimulation may not be performed only once, but may be performed whenever the user makes a selection or a predetermined period of times elapses, thereby making it possible to clearly ascertain the progress of the treatment.

The information on the disease input by the user in a state in which stimulation is applied to the user is different from the general intensity, frequency, and symptoms of the disease described above. In order to distinguish these information, in the present disclosure, information on the disease input by the user in a state in which stimulation is applied to the user is defined as the first disease information, and general information on the disease input by the user is defined as the second disease information. By adopting both the first disease information and the second disease information, a treatment protocol optimized for the user may be constructed or the treatment protocol may be modified to be optimized.

The user's biometric information measured by the measurement part may include brain waves, heartbeat, blood pressure, etc., and reflects the user's physical and psychological state. In the diagnosis step, changes in the body and mind that are not reflected in the user state information input by the user may be reflected for a more accurate diagnosis. In the treatment step, changes in the body and mind that are not reflected in the user state information input by the user may be reflected to construct a treatment protocol optimized for the user or modify the treatment protocol so as to be optimized. When measuring the user's brainwaves as the user biometric information, fast Fourier transform (FFT) analysis may be performed on the brainwaves, and the intensity and pattern of electrical stimulation may be modified by deriving the composition ratio of alpha waves among the brainwaves and determining the amount of change in the alpha waves. When measuring the heart rate as the user's biometric information, the amount of change in the heart rate may be measured or compared with a reference value, and the intensity and pattern of electrical stimulation may be modified accordingly.

In the process of using the treatment system using vagus nerve stimulation according to the present embodiment, the surrounding environment information is measured. The surrounding environment information includes temperature, humidity, fine dust, noise, light brightness, location, etc. By reflecting the influence of the surrounding environment in diagnosis and treatment, it is possible to enable an accurate diagnosis and optimized treatment even in a general home rather than a hospital where the diagnosis and treatment environment is controlled. As a specific method of reflecting the surrounding environment information in diagnosis and treatment, there is a way to quantify the surrounding environment information by converting the same into a stress index for the user.

This process may be divided into: an information collecting step of inputting, by the user, user information on the intensity and frequency of symptoms in a state in which stimulation for diagnosis is applied to the user's body through the electrode that generates electrical stimulation, and measuring the biometric information of the user; a treatment program designing step of determining the intensity and pattern of electrical stimulation on the basis of the measured biometric information and determining the treatment protocol including the treatment time and treatment intensity on the basis of the biometric information measured by the measurement part and the user information input by the input part, and; a treatment step of stimulating the vagus nerve by applying the designed treatment program to the electrode.

As such, by reflecting the information on the disease input by the user in a state in which stimulation for diagnosis or treatment is applied, and the measured biometric information and surrounding environment information of the user, together with general personal information of the user and general information on the disease, it is possible to construct a treatment protocol optimized for the user or modify the treatment protocol so as to be optimized. When other stimulation is added in addition to electrical stimulation to stimulate the vagus nerve, the stimulation combining a treatment protocol applies complex plurality of types of stimulation to the user, and the construction and modification of the treatment protocol proceed on the basis of the electrical stimulation to the vagus nerve. For example, when acoustic stimulation using sounds is added, the treatment protocol is constructed and modified on the basis of the electrical stimulation to the vagus nerve, and the acoustic stimulation is incidentally applied according to the construction and modification of the electrical stimulation.

In addition, the diagnosis and the construction and modification of the treatment protocol described in the present embodiment may be performed for each of the left ear and the right ear. The diagnosis and treatment may be performed on each ear not only when the treatment device is worn on only one ear, but also when the treatment device is worn on both ears.

In the present disclosure, the treatment protocol includes voltage, frequency, duty rate, and duty cycle for electrical stimulation, and is composed of a plurality of sessions. The modification of the treatment protocol may be performed by increasing or reducing each of the elements of the electrical stimulation described above, or by lengthening or shortening the length of the sessions. In addition, as for the modification of the treatment protocol, it is possible to reflect information obtained in the process of performing the treatment protocol to modify the entire treatment protocol to be performed subsequently, and it is also possible to reflect information obtained in the process of performing a previous session to modify a subsequent session in the process of performing the treatment protocol composed of the plurality of sessions.

Figure 4:
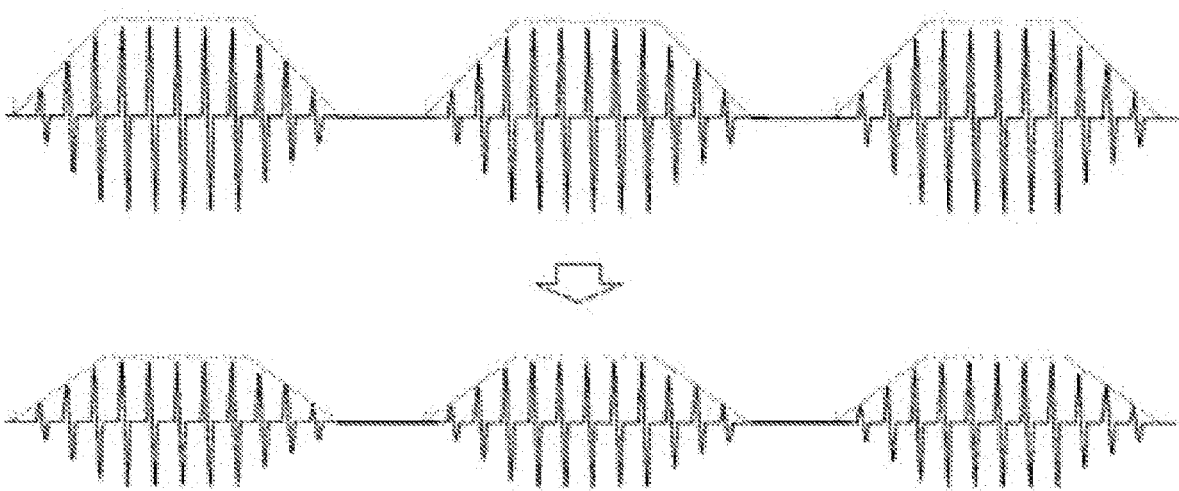
FIGS. 4 to 6 are views illustrating a state in which a treatment protocol is modified in the treatment system using vagus nerve stimulation according to the embodiment of the present disclosure.
Figure 5:
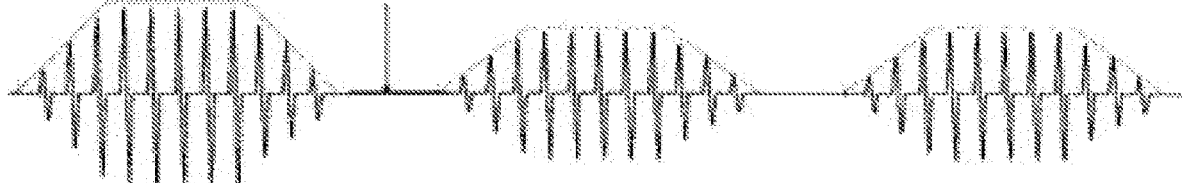
Figure 6:
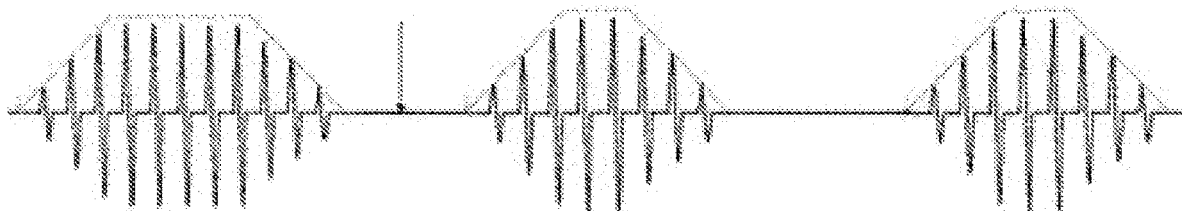

FIGS. 4 to 6 are views illustrating a state in which the treatment protocol is modified in the treatment system using vagus nerve stimulation according to the embodiment of the present disclosure.

The treatment system using vagus nerve stimulation has the treatment protocol in which electrical stimulation for stimulating the vagus nerve is repeatedly applied in a pattern of a predetermined intensity. The treatment system using vagus nerve stimulation according to the present embodiment reflects the input information of the user input while treatment is performed with the treatment protocol illustrated on the upper side of FIG. 4 and the measured biometric information and surrounding environment information of the user to modify the treatment protocol to the treatment protocol on the lower side in which the overall intensity of the treatment protocol to be performed subsequently is lowered.

In addition, by reflecting the input information of the user input while treatment is performed with the set treatment protocol and the measured biometric information and surrounding environment information of the user, the treatment protocol may be modified immediately. As illustrated in FIG. 5, in the case of the treatment protocol composed of the plurality of sessions to repeat stimulation of a predetermined pattern, by reflecting the input information of the user input while a first session is performed and the measured biometric information and surrounding environment information of the user, the stimulation intensity of sessions to be performed subsequently may be lowered. In addition, as illustrated in FIG. 6, by reflecting the input information of the user input while the first session is performed and the measured biometric information and surrounding environment information of the user, the length of the sessions to be performed subsequently may be reduced.

The form in which the treatment protocol is modified in the treatment system using vagus nerve stimulation according to the present disclosure is not limited thereto, and the length and intensity of the stimulation may be simultaneously changed or the pattern itself may be modified. The treatment protocol may be modified in more various forms when electrical stimulation is applied together with other stimulation.

Figure 7:
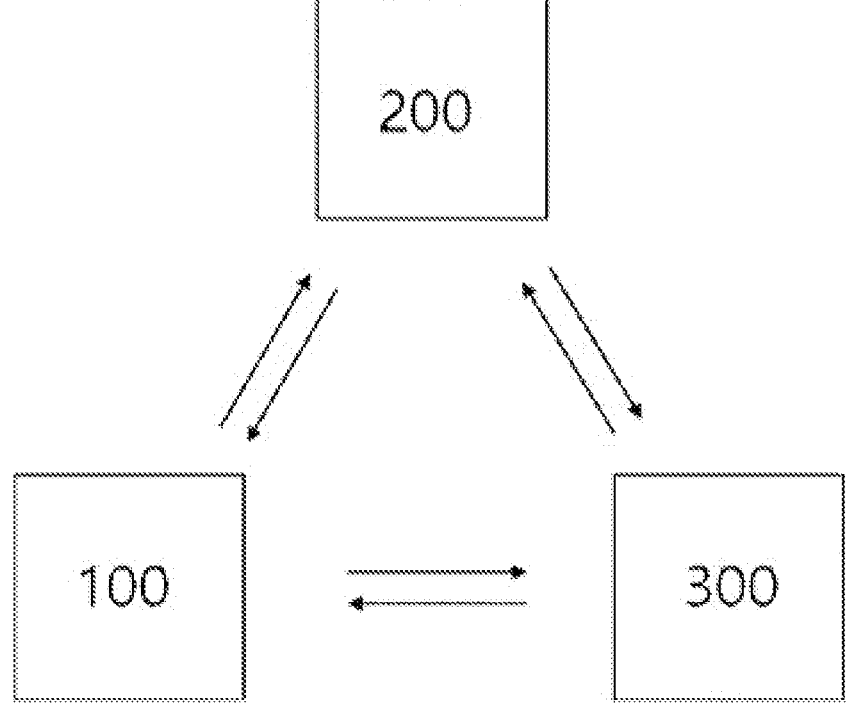
FIG. 7 is a schematic view illustrating a case in which the treatment system using vagus nerve stimulation according to the embodiment of the present disclosure includes an external server.

FIG. 7 is a schematic view illustrating a case in which the treatment system using vagus nerve stimulation according to the embodiment of the present disclosure includes an external server.

The treatment system using vagus nerve stimulation illustrated in FIG. 1 may be connected to the external server, and the illustrated present embodiment includes a treatment device part 100, a first server 200, and a second server 300. In this case, all or a part of the treatment system illustrated in FIG. 1 may be included in the treatment device part 100, and all or a part of the controller 20 may be functionally separated into controllers corresponding to the treatment device part 100, the first server 200, and the second server 300. For example, the treatment device part 100 may include a controller for constructing and modifying a treatment protocol. In this case, the process of constructing and modifying the treatment protocol may be performed in the first server 200 or the second server 300, and the controller of the treatment device part 100 may be a configuration that simply receives and applies the constructed and modified treatment protocol. When the process of constructing and modifying the treatment protocol is performed only in the first server 200 or the second server 300, the configuration of the controller included in the treatment device part 100 can be simplified, but there is a disadvantage in that it is difficult to immediately reflect user's input information or biometric information measurement results. Thus, it is preferable to distribute functions so that the controller included in the treatment device part 100 is configured to construct and modify the treatment protocol at a general level, and the first server 200 or the second server 300 constructs and modifies the treatment protocol at a more complex level.

The treatment device part 100 according to the present embodiment includes a treatment device including an electrode for stimulating the vagus nerve, an input device for the user to input information, a measuring device for measuring biometric information of the user, and an environment measuring device for measuring surrounding environment information of the user. The treatment device, the input device, the measuring device, and the environment measuring device may be included in one device, or a part or all thereof may be distributed in separate devices. In particular, the measuring device and the environment measuring device may be configured as a wearable device acting on the human body or may be configured to transmit and receive information in connection with the wearable device.

In the present embodiment, although the first server 200 and the second server 300 are described as being separate components, only one of the first server 200 or the second server 300 may be provided, or a single server in which the functions of the first server 200 and the second server 300 are integrated may be provided.

In the present embodiment, the first server 200 is a server managed by a manufacturer of a treatment device using vagus nerve stimulation, and the second server 300 is a server managed by a hospital where the user using the treatment device using vagus nerve stimulation is treated.

The first server 200 includes an artificial intelligence (AI)-based diagnosis and treatment algorithm, and performs diagnosis for a disease and construction and modification of the treatment protocol on the basis of input information of the user and information measured during use. However, such processes cannot be performed to the extent that has to be performed by a doctor, and various information on treatment may be provided within a range permitted by law. New content may be provided for the user by reflecting data accumulated through continuous research. For this purpose, a subscription system that provides information and content for the user on a regular basis may be adopted. The provided content includes a diagnosis stimulation protocol, a treatment stimulation protocol, training program sound sources and videos, etc. In addition, the first server 10 may provide video and sound content for diagnosis and video and sound content for treatment, may provide video and sound content for training, and preferably provides a community function so that multiple users can share their opinions and experiences. In addition, the first server 200 preferably encrypts and stores log data information so that the user does not need to repeatedly input personal information.

The second server 300 is connected to a medical terminal used by the doctor who is an expert, and is configured such that diagnosis by the doctor and modification of the treatment protocol are performed within a range that requires doctor's judgment. The medical terminal displays not only the user's information collected at the hospital, but also the user's biometric and disease-related information collected during treatment so that the doctor can make an accurate prescription. The hospital may receive the treatment device from the manufacturer of the treatment device, sell the device to the user who is a patient, and manage the device. This can increase patient management and treatment efficiency, and apply accumulated various clinical information to research.

While the exemplary embodiments of the present disclosure have been described above, the embodiments are only exemplary of the present disclosure, and it will be understood by those skilled in the art that the present disclosure can be modified in various forms without departing from the technical spirit of the present disclosure. Therefore, the scope of the present disclosure should be determined on the basis of the descriptions in the appended claims, not any specific embodiment, and all equivalents thereof should belong to the scope of the present disclosure.

The invention claimed is:

1. A treatment system using vagus nerve stimulation, the treatment system comprising:
   a treatment part including an electrode configured to be worn on at least one of the left and right ears and configured to generate electrical stimulation on the vagus nerve in the auricle;
   a controller configured to transmit an electrical stimulation signal for generating the electrical stimulation to the treatment part;
   an input part configured to allow a user to input user information;
   an environment measurement part configured to measure surrounding environment information;
   a measurement part configured to measure biometric information on the user,
   wherein the controller adjusts an intensity and a pattern of the electrical stimulation on the basis of the biometric information measured by the measurement part, and
   wherein the controller adjusts a treatment protocol including treatment time and treatment intensity on the basis of the biometric information measured by the measurement part and the user information input by the input part and a stress index converted from the surrounding environment information measured by the environment measurement part.

2. The treatment system of claim 1, wherein the measurement part measures brainwaves of the user, and the controller adjusts the intensity and pattern of the electrical stimulation on the basis of the measured brainwaves.

3. The treatment system of claim 2, wherein the controller performs fast Fourier transform (FFT) analysis on the brainwaves, and adjusts the electrical stimulation on the basis of an amount of change in the brainwaves obtained by comparing a composition ratio of the brainwaves.

4. The treatment system of claim 1, wherein the measurement part measures a heart rate of the user, and the controller adjusts the intensity and pattern of the electrical stimulation on the basis of the measured heart rate.

5. The treatment system of claim 4, wherein the controller adjusts the intensity of the electrical stimulation by comparing heart rate variability with a reference value.

6. The treatment system of claim 1, wherein the user information includes disease information related to a disease and other general information,
   the disease information includes first disease information on an intensity and a frequency of symptoms input while the electrical stimulation is applied and second disease information as other disease-related information, and
   the controller adjusts the treatment protocol on the basis of the first disease information.

7. The treatment system of claim 6, wherein a treatment process is composed of a plurality of sessions, and the treatment protocol of a subsequent session is adjusted on the basis of the first disease information input by the user in a previous session.

8. The treatment system of claim 1, wherein the treatment part further includes an acoustic device configured to generate a sound, and the controller transmits a sound signal to the acoustic device, and
   the controller derives a hearing loss pattern and a hearing loss frequency on the basis of the information input by the user in a state in which a sound is applied, and adjusts an attenuation frequency and a width of a bandpass filter for treatment of hearing loss.

9. The treatment system of claim 1, wherein the environment measurement part is installed in a wearable device.

10. The treatment system of claim 1, wherein the measurement part is installed in the treatment part worn on the user's ear.

11. The treatment system of claim 1, wherein the measurement part is installed in a wearable device.

12. A method of operating a treatment system using vagus nerve stimulation, the method comprising:
   an information collecting step of inputting by a user, user information on an intensity and a frequency of symptoms in a state in which stimulation for diagnosis is applied to the user's body through an electrode that is configured to be worn on at least one of the left and right ears and configured to generate electrical stimulation, and then measuring biometric information of the user and surrounding environment information;
   a treatment program designing step of determining an intensity and a pattern of the electrical stimulation on the basis of the measured biometric information, and determining a treatment protocol including treatment time and treatment intensity on the basis of the biometric information measured by a measurement part, and the user information input by an input part and a stress index converted from the surrounding environment information measured by an environment measurement part, and;
   a treatment step of stimulating the vagus nerve by applying a designed treatment program to the electrode.

13. A treatment system using vagus nerve stimulation, the treatment system comprising:
   a treatment part including an electrode configured to be worn on at least one of the left and right ears and configured to generate electrical stimulation on the vagus nerve in the auricle;
   a controller configured to transmit an electrical stimulation signal for generating the electrical stimulation to the treatment part;
   an input part configured to allow a user to input user information;
   an environment measurement part configured to measure surrounding environment information;
   a measurement part configured to measure biometric information on the user; and
   a server configured to send and receive data to and from the controller,
   wherein the server adjusts an intensity and a pattern of the electrical stimulation on the basis of the biometric information measured by the measurement part, and
   wherein the server adjusts a treatment protocol including treatment time and treatment intensity on the basis of the biometric information measured by the measurement part and the user information input by the input part and a stress index converted from the surrounding environment information measured by the environment measurement part to transmit the adjusted treatment protocol to the controller.

14. The treatment system of claim 13, wherein the server adjusts the intensity, the pattern, and the treatment protocol of the electrical stimulation through an artificial intelligence (AI)-based algorithm.

15. The treatment system of claim 13, wherein the server provides a diagnosis stimulation protocol and a treatment stimulation protocol.

16. The treatment system of claim 13, wherein the server provides video and sound content for diagnosis and video and sound content for treatment.

17. The treatment system of claim 13, wherein the server provides video and sound content for training.

18. The treatment system of claim 13, wherein the server is connected to a medical terminal used by an expert and adjusts the intensity, the pattern, and the treatment protocol of the electrical stimulation through the medical terminal.

19. The treatment system of claim 18, wherein the medical terminal displays personal information and disease-related information of the user.

\* \* \* \* \*